(12) United States Patent
Wang et al.

(10) Patent No.: US 11,931,187 B2
(45) Date of Patent: Mar. 19, 2024

(54) METHOD FOR PREDICTING CLINICAL SEVERITY OF A NEUROLOGICAL DISORDER BY MAGNETIC RESONANCE IMAGING

(71) Applicants: Chang Gung University, Taoyuan (TW); Chang Gung Memorial Hospital, Linkou, Taoyuan (TW); Chang Gung Medical Foundation Chang Gung Memorial Hospital at Keelung, Keelung (TW)

(72) Inventors: Jiun-Jie Wang, Taoyuan County (TW); Yi-Hsin Weng, Taoyuan (TW); Shu-Hang Ng, Taoyuan (TW); Jur-Shan Cheng, Taoyuan (TW); Yi-Ming Wu, Taoyuan (TW); Yao-Liang Chen, Taoyuan (TW); Wey-Yil Lin, Taoyuan (TW); Chin-Song Lu, Taoyuan (TW); Wen-Chuin Hsu, Taoyuan (TW); Chia-Ling Chen, Taoyuan (TW); Yi-Chun Chen, Taoyuan (TW); Sung-Han Lin, Taoyuan (TW); Chih-Chien Tsai, Taoyuan (TW)

(73) Assignees: Chang Gung Medical Foundation Chang Gung Memorial Hospital at Keelung, Keelung (TW); Chang Gung Memorial Hospital, Linkou, Keelung (TW); Chang Gung University, Taoyuan (TW)

( * ) Notice: Subject to any disclaimer, the term of this patent is extended or adjusted under 35 U.S.C. 154(b) by 518 days.

(21) Appl. No.: 15/923,929

(22) Filed: Mar. 16, 2018

(65) Prior Publication Data
US 2018/0263569 A1    Sep. 20, 2018

(30) Foreign Application Priority Data

Mar. 17, 2017 (TW) ................. 106108918

(51) Int. Cl.
*A61B 5/00* (2006.01)
*A61B 5/055* (2006.01)
*G06T 7/00* (2017.01)

(52) U.S. Cl.
CPC .......... *A61B 5/7275* (2013.01); *A61B 5/0042* (2013.01); *A61B 5/055* (2013.01);
(Continued)

(58) Field of Classification Search
CPC ... A61B 5/7275; A61B 5/0042; A61B 5/4088; A61B 5/4082; A61B 5/055;
(Continued)

(56) References Cited

U.S. PATENT DOCUMENTS 5,873,823 A * 2/1999 Eidelberg ................ G16Z 99/00
600/407
8,031,919 B2 * 10/2011 Eskildsen ............... G06T 7/149
382/128

(Continued)

*Primary Examiner* — Joseph M Santos Rodriguez
*Assistant Examiner* — Amy Shafqat
(74) *Attorney, Agent, or Firm* — Schwegman Lundberg & Woessner, P.A.

(57) ABSTRACT

A method for predicting clinical severity of a neurological disorder includes steps of: a) identifying, according to a magnetic resonance imaging (MRI) image of a brain, brain image regions each of which contains a respective portion of diffusion index values of a diffusion index, which results from image processing performed on the MRI image; b) for one of the brain image regions, calculating a characteristic parameter based on the respective portion of the diffusion index values; and c) calculating a severity score that represents the clinical severity of the neurological disorder of the brain based on the characteristic parameter of the one of the (Continued)

brain image regions via a prediction model associated with the neurological disorder.

5 Claims, 10 Drawing Sheets

(52) U.S. Cl.
CPC .......... *A61B 5/4082* (2013.01); *A61B 5/4088* (2013.01); *G06T 7/0012* (2013.01); *G06T 7/0016* (2013.01); *G06T 2207/10092* (2013.01); *G06T 2207/30016* (2013.01)

(58) Field of Classification Search
CPC ................ G06T 7/0016; G06T 7/0012; G06T 2207/10092; G06T 2207/30016; G16H 50/30
See application file for complete search history.

(56) References Cited

U.S. PATENT DOCUMENTS

| | | | | |
|---|---|---|---|---|
| 9,600,778 | B2* | 3/2017 | Sapiro | A61B 5/055 |
| 11,169,235 | B2* | 11/2021 | Zaiss | G01R 33/5608 |
| 2006/0017749 | A1* | 1/2006 | McIntyre | G16H 50/50 |
| | | | | 345/664 |
| 2008/0109171 | A1* | 5/2008 | McGraw | G01R 33/56341 |
| | | | | 702/19 |
| 2008/0159607 | A1* | 7/2008 | Littmann | A61B 6/463 |
| | | | | 382/128 |
| 2009/0279762 | A1* | 11/2009 | Tsukimoto | G01R 33/56341 |
| | | | | 382/131 |
| 2010/0080432 | A1* | 4/2010 | Lilja | G06T 7/0012 |
| | | | | 382/131 |
| 2011/0160543 | A1* | 6/2011 | Parsey | A61B 6/501 |
| | | | | 600/300 |
| 2011/0199084 | A1* | 8/2011 | Hasan | A61B 5/055 |
| | | | | 324/309 |
| 2011/0218253 | A1* | 9/2011 | Lange | A61K 45/00 |
| | | | | 514/789 |
| 2012/0143041 | A1* | 6/2012 | Hirsch | A61B 5/055 |
| | | | | 600/411 |
| 2013/0102877 | A1* | 4/2013 | Mori | G01R 33/5608 |
| | | | | 600/410 |
| 2013/0249553 | A1* | 9/2013 | Simonetti | G01R 33/56527 |
| | | | | 324/309 |
| 2013/0279771 | A1* | 10/2013 | Wang | G06T 7/0012 |
| | | | | 382/128 |
| 2014/0107521 | A1* | 4/2014 | Galan | A61B 5/0476 |
| | | | | 600/544 |
| 2014/0233819 | A1* | 8/2014 | Kim | G06T 7/11 |
| | | | | 382/131 |
| 2016/0035085 | A1* | 2/2016 | Peng | G06T 7/136 |
| | | | | 382/128 |
| 2016/0196393 | A1* | 7/2016 | Avinash | A61B 5/00 |
| | | | | 705/2 |
| 2016/0231410 | A1* | 8/2016 | Warfield | A61B 5/055 |
| 2016/0247302 | A1* | 8/2016 | Pan | G06T 11/005 |
| 2018/0321347 | A1* | 11/2018 | Wang | A61B 5/055 |
| 2019/0053726 | A1* | 2/2019 | Geva | A61B 5/048 |
| 2019/0183429 | A1* | 6/2019 | Sung | G06T 7/0012 |
| 2020/0107777 | A1* | 4/2020 | Javitt | G16H 50/20 |
| 2020/0265581 | A1* | 8/2020 | Prchkovska | A61B 5/743 |

* cited by examiner

METHOD FOR PREDICTING CLINICAL SEVERITY OF A NEUROLOGICAL DISORDER BY MAGNETIC RESONANCE IMAGING

CROSS-REFERENCE TO RELATED APPLICATION

This application claims priority of Taiwanese Patent Application No. 106108918, filed on Mar. 17, 2017, which is hereby incorporated by reference herein in its entirety.

FIELD

The disclosure relates to a method for predicting clinical severity of a neurological disorder, and more particularly to a method for predicting clinical severity of a neurological disorder by magnetic resonance imaging (MRI).

BACKGROUND

A conventional approach of evaluating clinical severity of a neurological disorder is based on a clinical neuropsychological assessment performed by a medical practitioner on a patient having the neurological disorder. However, the conventional approach is usually time consuming and impracticable in an outpatient scenario due to limited medical resources (e.g., time and manpower) for each outpatient.

Moreover, low compliance or adherence of patients with neurological disorders often adversely influences results of the clinical neuropsychological assessment. Furthermore, an objective approach to assess effectiveness of treatment for a neurological disorder in a specific patient is desired.

SUMMARY

Therefore, an object of the disclosure is to provide a method that is adapted for predicting clinical severity of a neurological disorder based on at least one magnetic resonance imaging (MRI) image which is associated with a brain and that can alleviate at least one of the drawbacks of the prior art.

According to the disclosure, the method is to be implemented by a computing device. The method includes steps of:
  a) identifying, based on said at least one MRI image, a plurality of brain image regions each of which contains a respective portion of diffusion index values of at least one diffusion index, which results from image processing performed on said at least one MRI image;
  b) for at least one of the brain image regions, calculating at least one characteristic parameter based on the respective portion of the diffusion index values of said at least one diffusion index; and
  c) calculating a severity score that represents the clinical severity of the neurological disorder of the brain based on said at least one characteristic parameter of said at least one of the brain image regions via a prediction model associated with the neurological disorder.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1A:
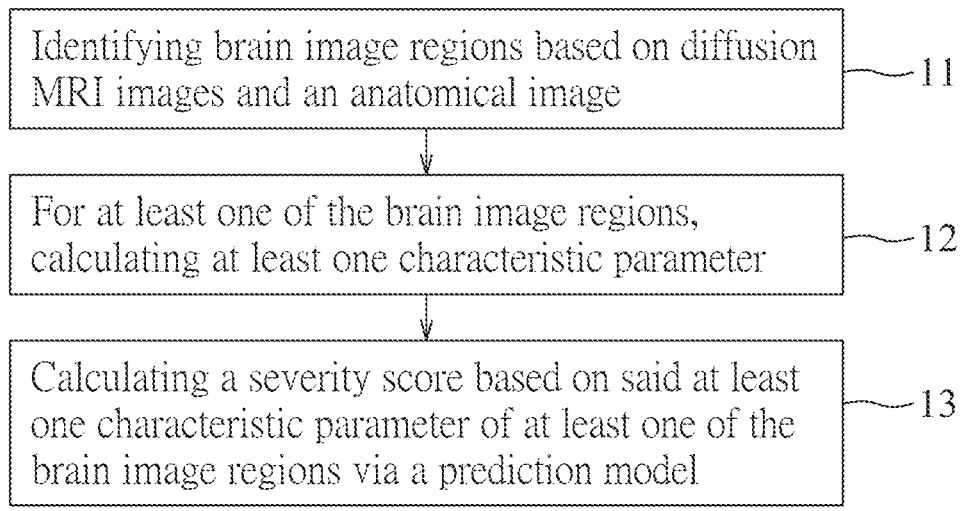
FIGS. 1(a) and 1(b) cooperate to illustrate a flow diagram of an embodiment of a method for predicting clinical severity of a neurological disorder by magnetic resonance imaging (MRI) according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1B:
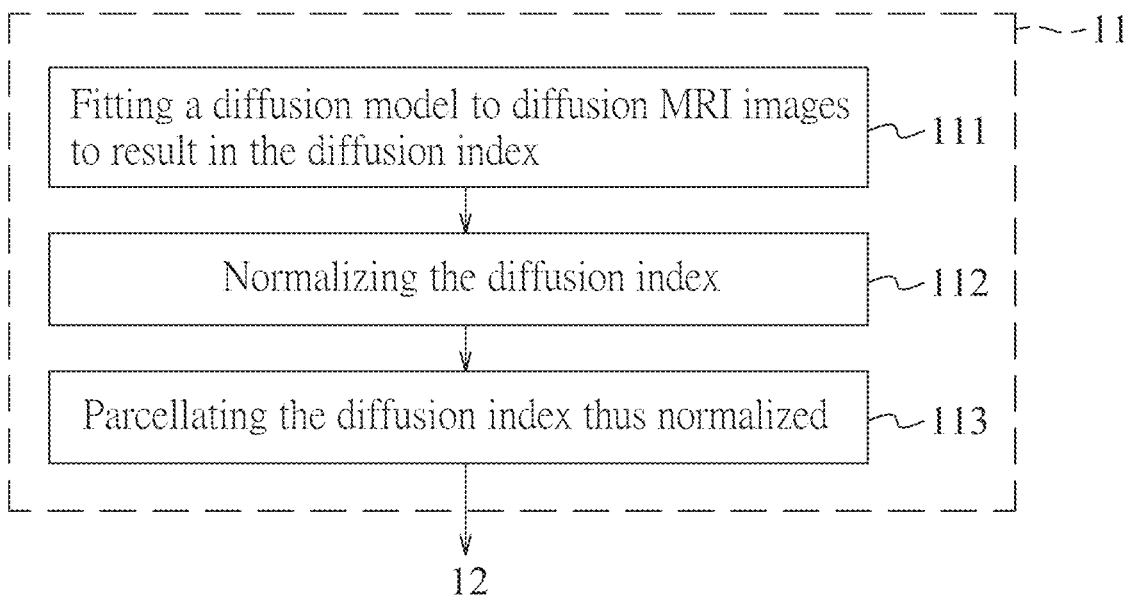
Figure 2:
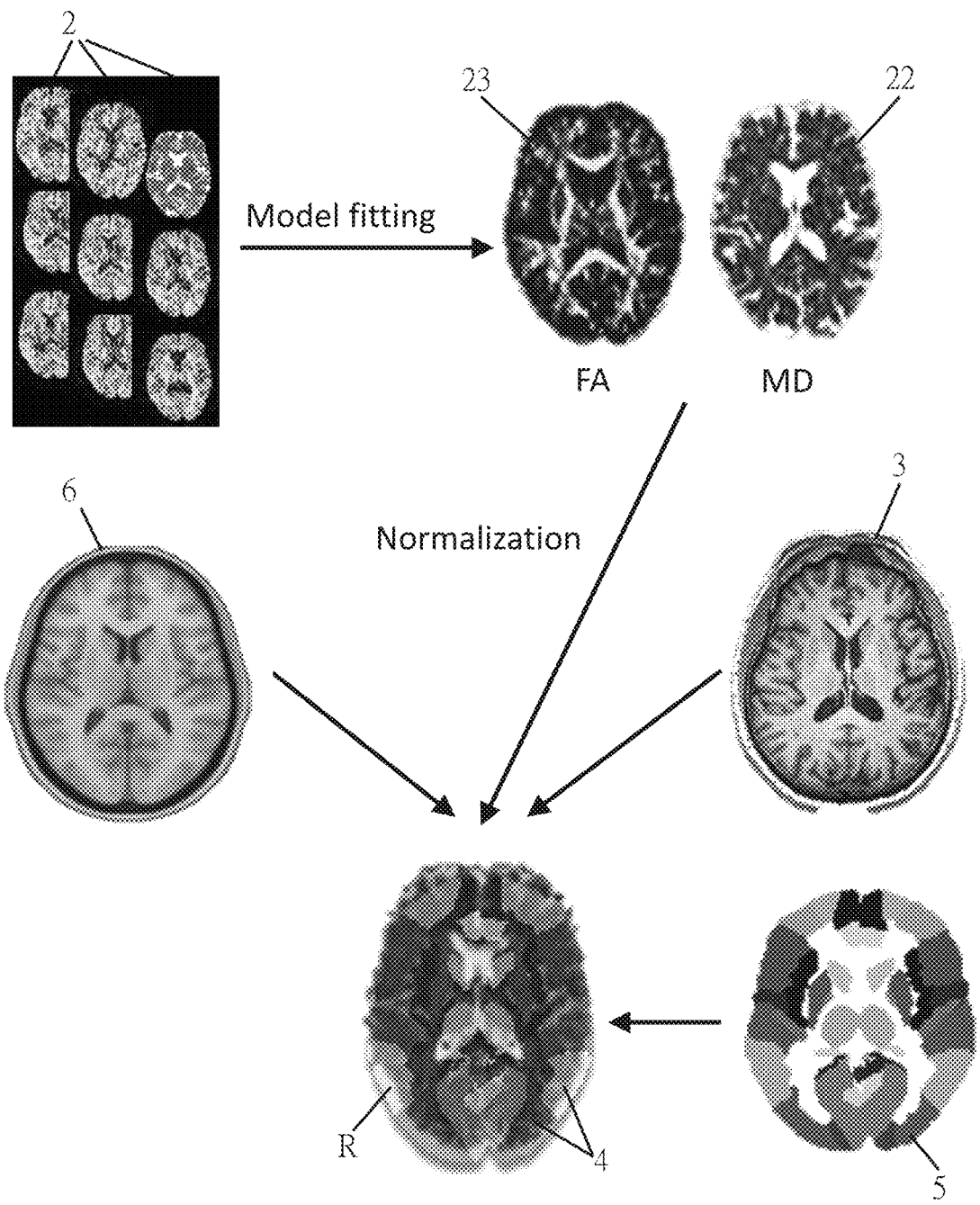
FIG. 2 is a schematic diagram illustrating an embodiment of a step of identifying a plurality of brain image regions based on a plurality of diffusion MRI images and an anatomical image in the method of this disclosure.

Referring to FIGS. 1A, 1B and 2, an embodiment of a method for predicting clinical severity of a neurological disorder based on at least one magnetic resonance imaging (MRI) image according to this disclosure is illustrated. The MRI image is associated with a brain, and is exemplified by a diffusion weighted image (DWI). In the method of this embodiment, predicting clinical severity of a neurological disorder is realized based on a plurality of diffusion MRI images 2 (for example, nine diffusion MRI images) and an anatomical image 3 with high contrast and high resolution. The neurological disorder may be a neurodegenerative disease, e.g., Parkinson's disease (PD), Alzheimer's disease (AD) or the like, or a neurodevelopmental disorder, e.g., cerebral palsy (CP) or the like, but is not limited thereto. The method is to be implemented by a computing device having computational capability, such as a workstation computer, a personal computer, a tablet computer, or the like, but is not limited thereto. The method includes the following steps 11-13.

Referring to FIGS. 1(a) and 1 (b), step 11 includes sub-steps 111-113 described as follows.

In sub-step 111, the computing device performs image processing on the diffusion MRI images 2 to result in at least one diffusion index. Specifically, said at least one diffusion index is generated by fitting a diffusion model to the diffusion MRI images 2. Said at least one diffusion index is defined by a plurality of diffusion index values. In one embodiment, said at least one diffusion index may be formatted as an image, and an individual one of the diffusion index values is implemented to be a pixel value of a pixel in the aforementioned image. The image processing (i.e., the diffusion model adopted for fitting) is one of diffusion tensor imaging (DTI), diffusion kurtosis imaging (DKI), neurite orientation dispersion and density imaging (NODDI), and the AxCaliber technique which is an expansion to the composite hindered and restricted model of diffusion (CHARMED) framework. Specifically speaking, for each of the brain image regions 4, said at least one diffusion index resulting from DTI is one of fractional anisotropy (FA), mean diffusivity (MD), radial diffusivity (RD) and axial diffusivity (AXD); said at least one diffusion index resulting from DKI is one of kurtosis fractional anisotropy (KFA), mean kurtosis (MK), radial kurtosis (Kr) and axial kurtosis (Ka); said at least one diffusion index resulting from NODDI is one of intra-cellular volume fraction (Ficvf), cerebrospinal fluid volume fraction (Fiso), fitting objective function values (Fmin), concentration parameter of Watson distribution (Fkappa) and orientation dispersion index (ODI); and said at least one diffusion index resulting from the AxCaliber technique is one of signal decay of the hindered diffusion fraction of water molecules (Eh) and signal decay of the restricted diffusion fraction of water molecules (Er). For example, two diffusion indexes that are respectively MD and FA can be obtained by fitting DTI to the diffusion MRI images 2, and can be formatted as two images which are simply referred to as MD (22) and FA (23) herein, respectively.

Subsequently, said at least one diffusion index is normalized based on the anatomical image 3 and a structural template 6 (see FIG. 2) in sub-step 112, and is then parcellated through automatic whole-brain parcellation in sub-step 113 according to a standard brain parcellation template 5, e.g., an automated anatomical labeling (AAL) template as shown in FIG. 2, so that a plurality of brain image regions 4 are identified thereon. In this embodiment, the brain image regions 4 are one hundred and sixteen in number, but implementation of the number of the brain image regions 4 is not limited to what are disclosed herein. Each of the brain image regions 4 contains a respective portion of the diffusion index values (i.e., the pixel values of pixels corresponding to the brain image region) of said at least one diffusion index.

It should be noted that the normalizing of said at least one diffusion index is performed spatially, and implementation thereof is not limited to what are disclosed herein and may vary in other embodiments.

In step 12, for each of the brain image regions 4, at least one characteristic parameter is calculated based on the respective portion of the diffusion index values of said at least one diffusion index, where the respective portion of the diffusion index values corresponds to the brain image region. For each of the brain image regions 4, said at least one characteristic parameter includes a statistical value of the respective portion of the diffusion index values corresponding to the brain image regions 4. In this embodiment, the statistical value may be implemented to be one of a mean and a percentile, e.g., a $10^{th}$ percentile, a $50^{th}$ percentile, a $90^{th}$ percentile or the like, but is not limited thereto.

In step 13, a severity score that represents the clinical severity of the neurological disorder of the brain is calculated based on the characteristic parameter(s) of at least one of the brain image regions 4 via a prediction model that is trained in advance and that is associated with the neurological disorder. In this embodiment, the prediction model is implemented by a regression model, but is not limited thereto.

In one embodiment, the prediction model is implemented by a linear regression model, and the severity score is calculated for the purpose of predicting an evaluation score which would be obtained by grading the clinical severity of the neurological disorder of the brain with a rating scale (e.g., a Unified Parkinson's disease rating scale) in a time period during which said at least one MRI image of the brain is generated. Specifically speaking, in order to predict clinical severity of a neurological disorder, a plurality of training samples corresponding to this neurological disorder are collected for training the prediction model. That is to say, for each individual, a plurality of diffusion MRI images 2 and an anatomical image 3 that are associated with a brain of the individual, and an evaluation score that is obtained by manually filling in an assessment form related to the rating scale are collected to serve as a sample set. Thereafter, according to steps 11 and 12 mentioned previously, for each individual, the characteristic parameters corresponding to the sample set are thereby calculated, and a combination of the characteristic parameters and the evaluation score serves as one of the training samples and is utilized to train the prediction model (i.e., the linear regression model) by a statistical approach, such as a stepwise regression or a combination of regression with cross-validation.

For example, for each individual, one hundred and sixteen brain image regions 4 are identified by AAL. Fifteen characteristic parameters are calculated for each of the brain image regions 4. For each of the brain image regions 4, the fifteen characteristic parameters include a $50^{th}$ percentile of index values of FA, a $10^{th}$ percentile of the index values of FA, a $90^{th}$ percentile of the index values of FA, a $50^{th}$ percentile of index values of MD, a $10^{th}$ percentile of the index values of MD, a $90^{th}$ percentile of the index values of MD, a $50^{th}$ percentile of index values of RD, a $10^{th}$ percentile of the index values of RD, a $90^{th}$ percentile of the index values of RD, a $50^{th}$ percentile of index values of AXD, a $10^{th}$ percentile of the index values of AXD, a $90^{th}$ percentile of the index values of AXD, a $50^{th}$ percentile of index values of MK, a $10^{th}$ percentile of the index values of MK, and a $90^{th}$ percentile of the index values of MK. Therefore, one thousand seven hundred and forty characteristic parameters are calculated in total for each individual. A portion of the characteristic parameters will be automatically selected by the statistical approach from the one thousand seven hundred and forty characteristic parameters to serve as independent variables $\{X_{1i}|i=1, 2, \ldots, N\}$ of a linear regression model, i.e., $Y_1=\beta_{10}+\beta_{11}X_{11}+\beta_{12}X_{12}+\ldots+\beta_{1N}X_{1N}$, where N is a number of characteristic parameters included in the portion of the characteristic parameters thus selected, $\{\beta_{1i}|i=1, 2, \ldots, N\}$ are regression coefficients determined by the statistical approach, and $Y_1$ is a dependent variable, i.e., the severity score to be eventually calculated to represent the clinical severity of the neurological disorder of the brain of the individual.

Consequently, by substituting the portion of the characteristic parameters calculated in step 12 $\{X_{1i}|i=1, 2, \ldots, N\}$ into the linear regression model previously mentioned, the severity score that is associated with the brain in a time period during which the diffusion MRI images 2 of the brain is generated can be calculated to predict the evaluation score that would be obtained through the assessment form related to the rating scale. In other words, only the diffusion MRI images 2 and the anatomical image 3 are required for an automatic determination of the severity score, without the requirement of manually filling in the assessment form.

It is worth to note that, when utilizing the prediction model to calculate the severity score and when the number of characteristic parameters included in the portion of the characteristic parameters thus selected is less than one thousand seven hundred and forty, only the portion of the characteristic parameters thus selected need to be calculated, without the requirement of calculating all one thousand seven hundred and forty characteristic parameters.

Figure 3A:
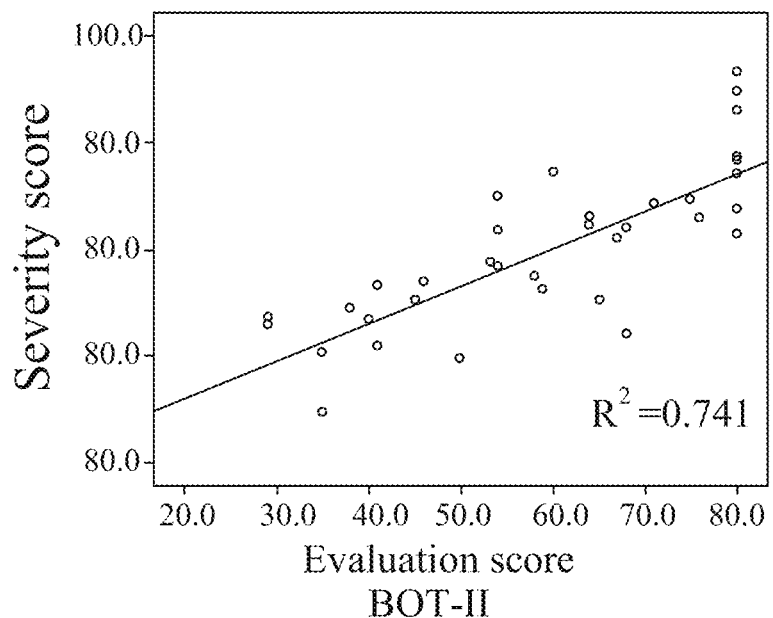
FIGS. 3(a) and 3(b) are scatter plots exemplifying goodness of fit of a linear regression model for determining clinical severity of cerebral palsy (CP) in Bruininks-Oseretsky Test of Motor Proficiency, Second Edition (BOT-II) and Functional Independence Measure for Children (WeeFIM) according to the method of this disclosure.
Figure 3B:
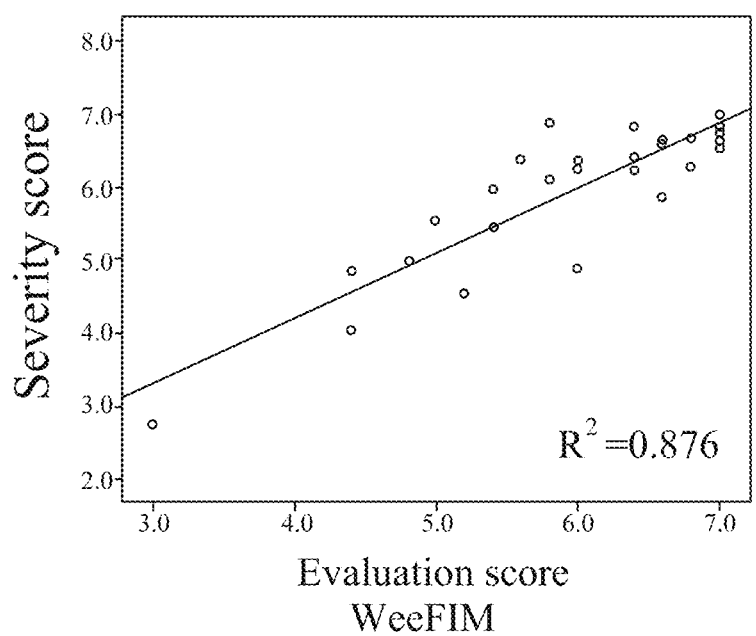

Referring to FIGS. 3(a) and 3(b), to verify effectiveness of the method of this disclosure, a plurality of samples each of which is associated with a CP patient are collected and analyzed. Specifically speaking, each of the samples includes a plurality of diffusion MRI images 2 and an anatomical image 3 of the CP patient, an evaluation score obtained through filling in an assessment form of Bruininks-Oseretsky Test of Motor Proficiency, second edition (BOT-II) by the CP patient at about the same time the diffusion MRI images 2 and the anatomical image 3 (referred to as "the images" hereinafter) are generated (the time difference should be insignificant to the outcome of the assessment, i.e., the time the images are generated and the time the assessment is filled in should belong to the same stage of progression in the patient with cerebral palsy), and an evaluation score obtained through filling in an assessment form of Functional Independence Measure for Children (WeeFIM) by the CP patient at about the same time. Subsequently, an adjusted $R^2$ is utilized to inspect the goodness of fit of the prediction model mentioned above (i.e., the linear regression model) for predicting the evaluation scores in BOT-II and WeeFIM. As shown in FIG. 3(a), severity scores calculated by the linear regression model of this disclosure based on the samples thus collected are significantly relevant to evaluation scores obtained in BOT-II, and an adjusted $R^2$ calculated based on the severity scores and the evaluation scores is equal to 0.741. As shown in FIG. 3(b), the severity scores calculated by the linear regression model of this disclosure based on the samples thus collected are significantly relevant to evaluation scores obtained in WeeFIM, and an adjusted $R^2$ calculated based on the severity scores and the evaluation scores is equal to 0.876. Therefore, the linear regression model of this disclosure is proven to be suitable for estimating clinical severity of CP of a brain at a time the images of the brain are generated.

Figure 4A:
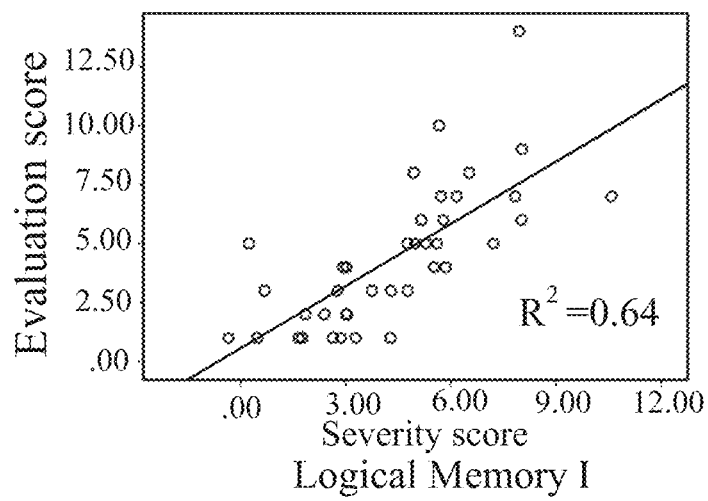
FIGS. 4(a) to 4(c) are scatter plots exemplifying goodness of fit of a linear regression model for predicting clinical severity of Alzheimer's disease (AD) in Wechsler Memory Scale—Revised, according to the method of this disclosure.
Figure 4B:
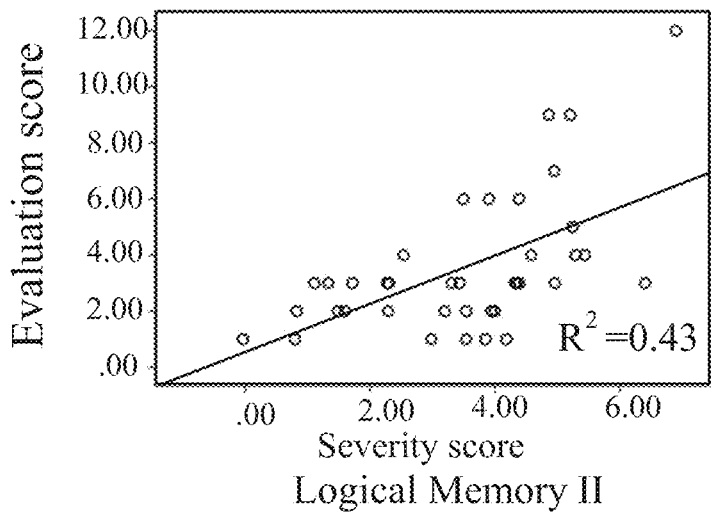
Figure 4C:
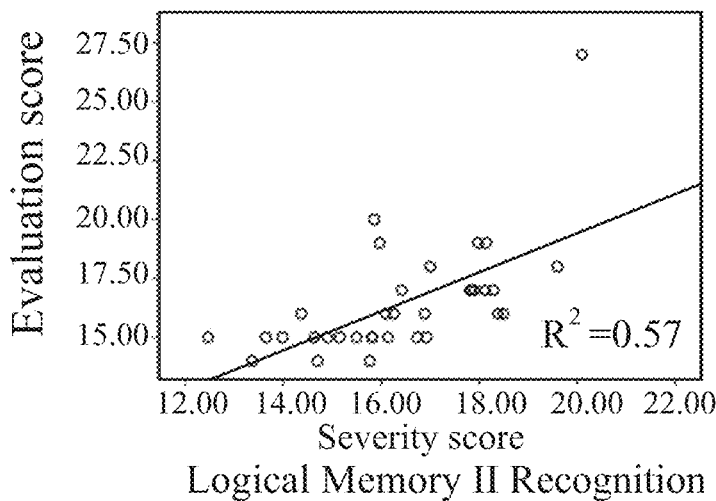

Similarly, a plurality of samples, each of which is associated with an AD patient, are collected and analyzed. Specifically speaking, each of the samples includes a plurality of diffusion MRI images 2 and an anatomical image 3 of the AD patient, and evaluation scores obtained through filling in assessment forms of Logical Memory I, Logical Memory II, and Logical Memory II Recognition rating scales in Wechsler Memory Scale Revised at about the same time the images are generated (the time difference should be insignificant to the outcome of the assessment). Subsequently, an adjusted $R^2$ is utilized to inspect the goodness of fit of the prediction model mentioned above (i.e., the linear regression model) for predicting the evaluation scores in Logical Memory I, Logical Memory II, and Logical Memory II Recognition rating scales in Wechsler Memory Scale Revised. Referring to FIGS. 4(a) to 4(c), it is evident that the linear regression model of this disclosure is also suitable for utilization to estimate clinical severity of AD of a brain at the time the images of the brain are generated. In each of FIGS. 4(a) to 4(c), an adjusted $R^2$ is calculated to be equal to a respective one of 0.64, 0.43 and 0.57.

Figure 5A:
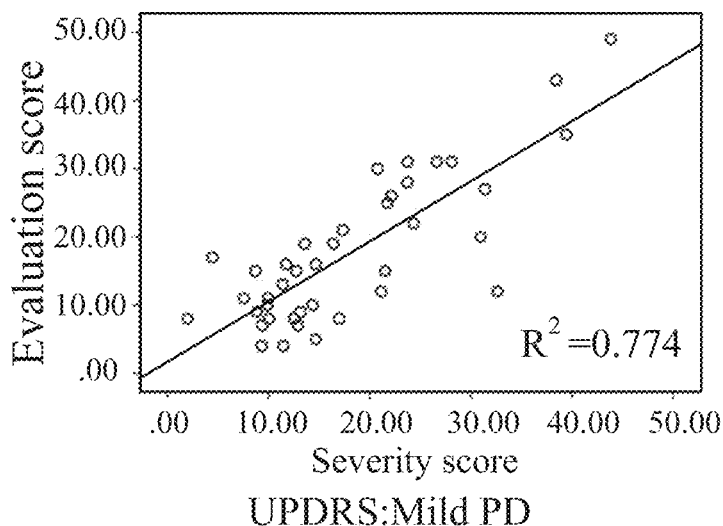
FIGS. 5(a) to 5(c) are scatter plots exemplifying goodness of fit of a linear regression model for predicting clinical severity of Parkinson's disease (PD) in Unified Parkinson's Disease Rating Scale (UPDRS) according to the method of this disclosure.
Figure 5B:
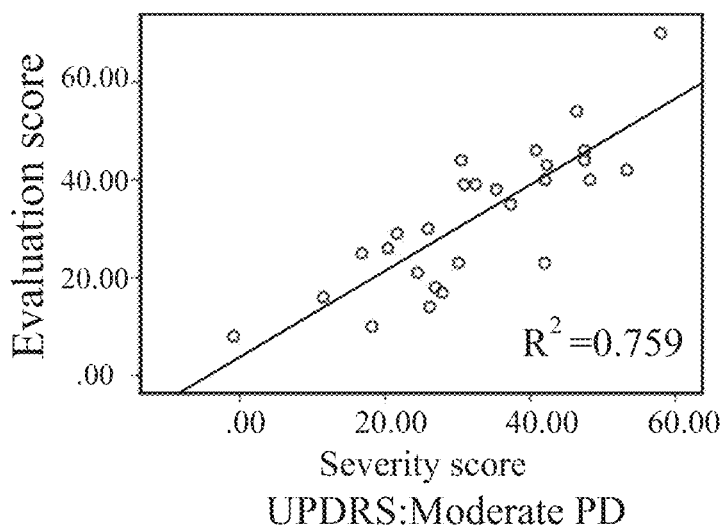
Figure 5C:
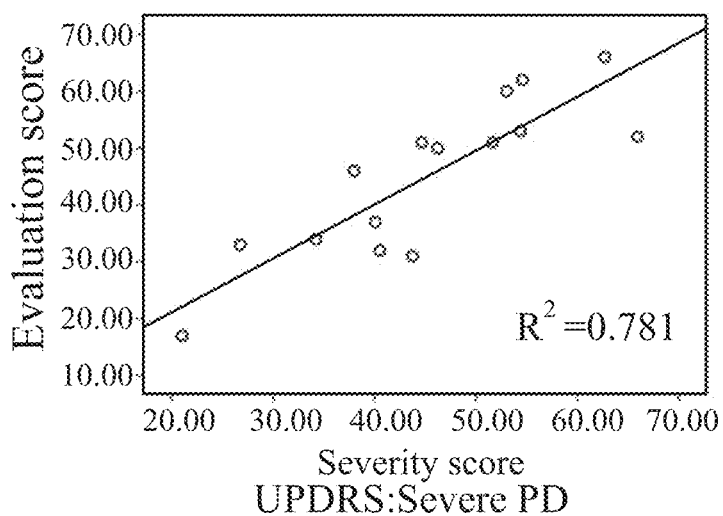
Figure 6A:
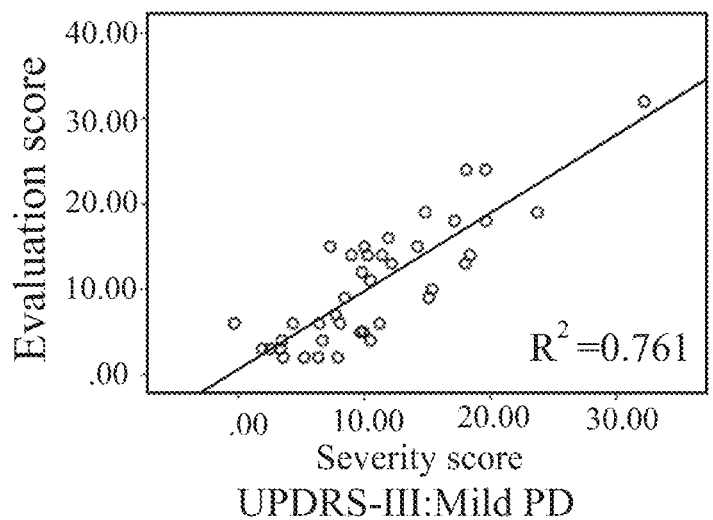
FIGS. 6(a) to 6(c) are scatter plots exemplifying goodness of fit of another linear regression model for predicting clinical severity of PD in Unified Parkinson's Disease Rating Scale—motor domain (UPDRS-III) according to the method of this disclosure.
Figure 6B:
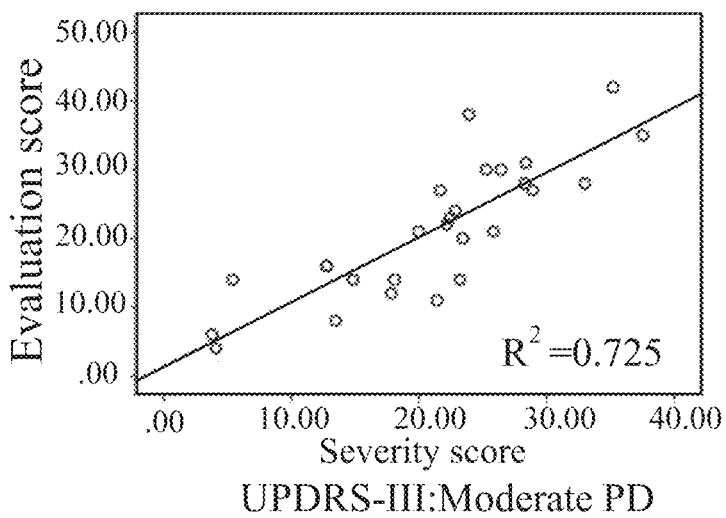
Figure 6C:
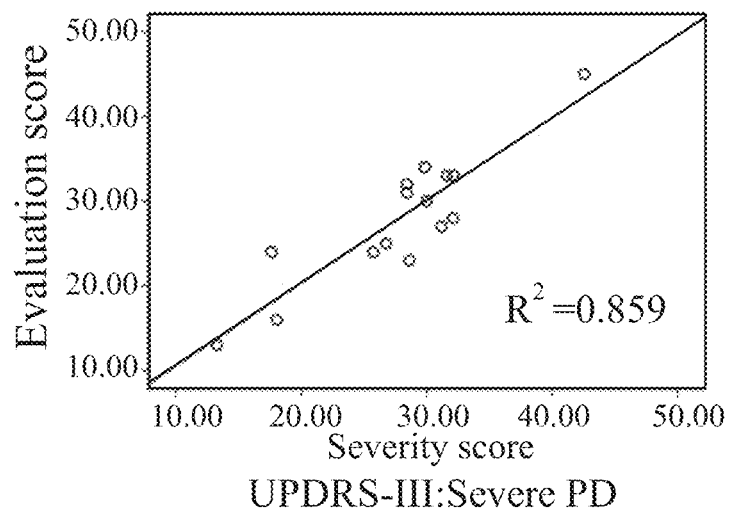

Similarly, a plurality of samples, each of which is associated with a PD patient, are collected and analyzed. Specifically speaking, each of the samples includes a plurality of diffusion MRI images 2 and an anatomical image 3 of the PD patient, and evaluation scores obtained through filling in assessment forms of mild, moderate and sever rating scales in Unified Parkinson's Disease Rating Scale (UPDRS) at about the same time the images are generated (the time difference should be insignificant to the outcome of the assessment). Subsequently, an adjusted $R^2$ is utilized to inspect the goodness of fit of the prediction model mentioned above (i.e., the linear regression model) for predicting the evaluation scores in the mild, moderate and sever rating scales in UPDRS (i.e., MHY 1, 2 and 3 respectively). Referring to FIGS. 5(a) to 5(c), it is evident that the linear regression model of this disclosure is also suitable for being utilized to estimate clinical severity of PD of a brain at the time the images of the brain are generated. In each of FIGS. 5(a) to 5(c), an adjusted $R^2$ is calculated to be equal to a respective one of 0.774, 0.759 and 0.781. Likewise, referring to each of FIGS. 6(a) to 6(c), an adjusted $R^2$ is calculated to be equal to a respective one of 0.761, 0.725 and 0.859, and is utilized to inspect the goodness of fit of the prediction model mentioned above (i.e., the linear regression model) for predicting the evaluation score that would otherwise be obtained through filling in an assessment form of a respective one of mild, moderate and sever rating scales in Unified Parkinson's Disease Rating Scale—motor domain (UPDRS-III).

Another embodiment of the method of this disclosure is adapted to estimate a prognosis of a neurological disorder, i.e., a forecast of clinical severity of the neurological disorder in the future, by using the prediction model, i.e., the linear regression model. Specifically speaking, a plurality of sample sets associated with the neurological disorder are collected so as to be utilized to train the linear regression model of the method. Each of the sample sets corresponds to a patient, and includes a plurality of diffusion MRI images 2 and an anatomical image 3 of the patient's brain generated at a first time instance, a first evaluation score obtained through the patient filling in an assessment form around the first time instance, and a second evaluation score obtained through the patient filling in the assessment form at a second time instance. It is worth to note that the first time instance at which the diffusion MRI images 2 and the anatomical image 3 of the brain are generated, and the time the patient fills in the assessment form from which the first evaluation score is obtained belong to the same stage of progression in the patient's neurological disorder, and that the second time instance is later than the first time instance (e.g., the second time instance is later than the first time instance by one year). By performing the aforementioned steps 11 and 12, for each of the sample sets, characteristic parameters are calculated for a corresponding patient. Based on the characteristic parameters of the brain image regions 4 and based on a predetermined first severity score (implemented by the first evaluation score) that represents the clinical severity of the neurological disorder of the brain at the first time instance, a second severity score is calculated, wherein the second severity score represents the projected clinical severity of the neurological disorder of the brain at the second time instance. More specifically, based on the characteristic parameters of the brain image regions 4, a score difference which is a predicted variation in the first severity score from the first time instance to the second time instance is calculated, and then the second severity score is calculated by summing the first severity score and the score difference. For each of the sample sets, a combination of the characteristic parameters and the score difference will be utilized to serve as a training sample to train the linear regression model by the statistical approach. In other words, a portion of characteristic parameters will be automatically selected by the statistical approach from the one thousand seven hundred and forty characteristic parameters to serve as independent variables $\{X_{2i}|i=1, 2, \ldots, N\}$ of a linear regression model, i.e., $Y_2=\beta_{20}+\beta_{21}X_{21}+\beta_{22}X_{22}+ \ldots +\beta_{2N}X_{2N}$, where N is a number of the portion of the characteristic parameters thus selected, $\{\beta_{2j}|j=1, 2 \ldots, N\}$ are regression coefficients determined by the statistical approach, and $Y_2$ is a dependent variable, i.e., the score difference to be eventually calculated to represent the predicted variation in the first severity score from the first time instance to the second time instance.

Consequently, by substituting the portion of the characteristic parameters calculated in step 12 $\{X_{2i}|i=1, 2, \ldots, N\}$ into the linear regression model previously mentioned, the score difference can be obtained, and the second severity score can be calculated by summing the first severity score and the score difference thus obtained. That is to say, the second severity score can be calculated based the linear regression model so as to predict the second evaluation score, which would be obtained through filling in the assessment form at the second time instance, and the patient is only required to undergo an MRI procedure for generation of the diffusion MRI images 2 and to fill in the assessment form to obtain the first evaluation score at the first time instance.

As a result, a medical practitioner may objectively make a determination as to whether a treatment performed on an examinee effectively improves the neurological disorder.

Figure 7A:
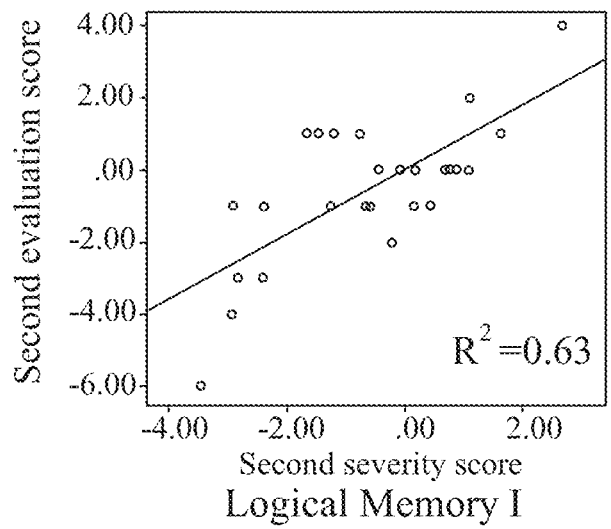
FIGS. 7(a) to 7(c) are scatter plots exemplifying goodness of fit of a linear regression model for predicting a prognosis of AD in Wechsler Memory Scale—Revised according to the method of this disclosure.
Figure 7B:
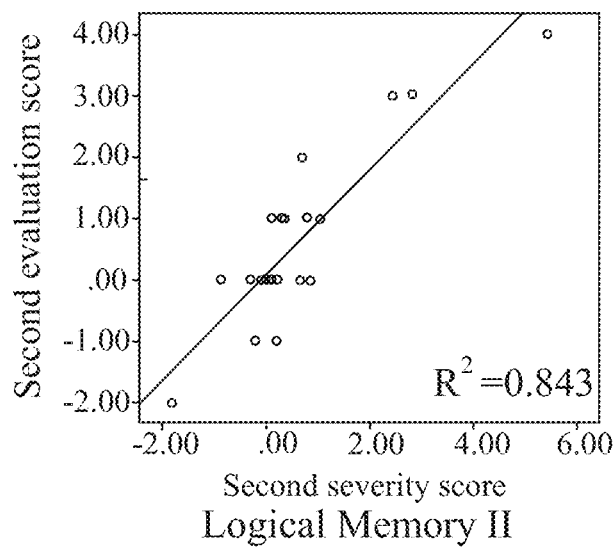
Figure 7C:
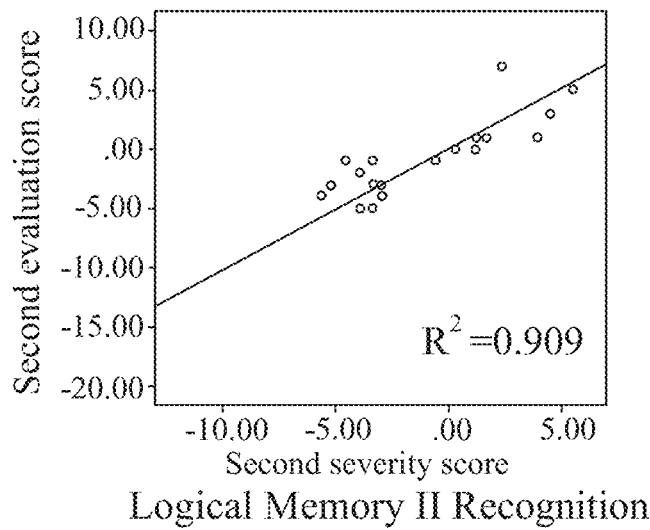

Referring to FIGS. 7(a) to (c), to verify effectiveness of the method for estimating prognosis of this disclosure, a plurality of samples, each of which is associated with an AD patient, are collected and analyzed. Specifically speaking, each of the samples includes a plurality of diffusion MRI images 2 and an anatomical image 3 of the AD patient generated at a first time instance, first evaluation scores obtained through filling in, by the AD patient about the same time as the first time instance, assessment forms of Logical Memory I, Logical Memory II, and Logical Memory II Recognition rating scales in Wechsler Memory Scale Revised, and second evaluation scores obtained through filling in, by the AD patient at a second time instance, assessment forms of Logical Memory I, Logical Memory II, and Logical Memory II Recognition rating scales in Wechsler Memory Scale Revised. The second time instance is later than the first time instance by one year. The second severity scores are calculated by the linear regression model of this disclosure based on the samples thus collected and on the first evaluation scores. Subsequently, an adjusted $R^2$ is utilized to inspect the goodness of fit of the predication model mentioned above (i.e., the linear regression model) for predicting the second evaluation scores in Logical Memory I, Logical Memory II, and Logical Memory II Recognition rating scales. Referring to FIGS. 7(a) to 7(c), it is evident that the linear regression model of this disclosure is also suitable for utilization in estimating a prognosis of AD of a brain previously examined. In each of FIGS. 7(a) to 7(c), a calculated adjusted $R^2$ is equal to a respective one of 0.63, 0.843 and 0.909.

Figure 8A:
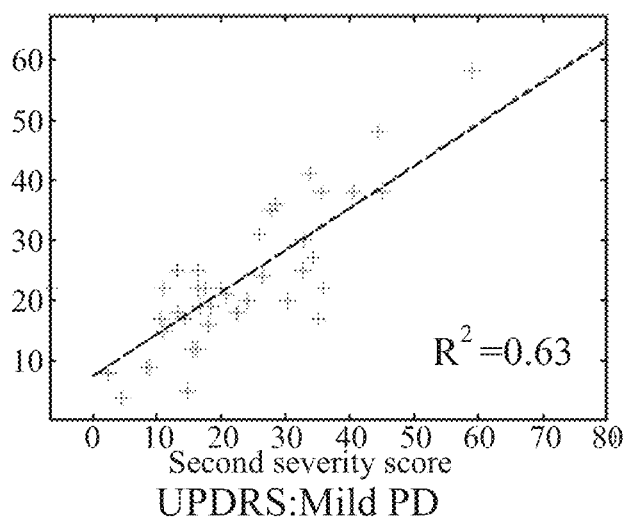
FIGS. 8(a) to 8(c) are scatter plots exemplifying goodness of fit of a linear regression model for predicting a prognosis of PD in UPDRS according to the method of this disclosure.
Figure 8B:
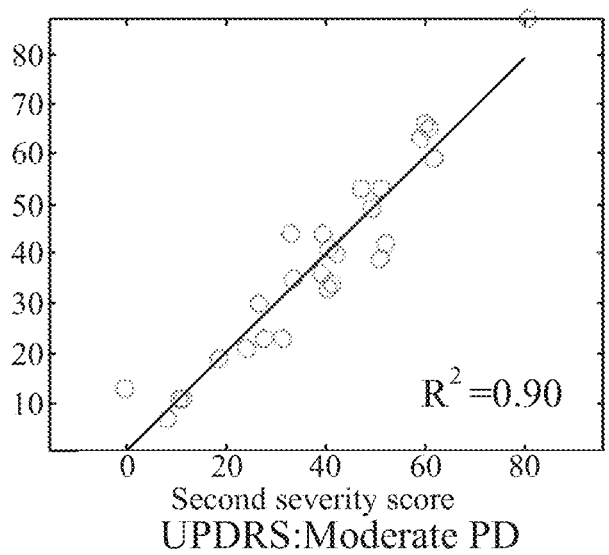
Figure 8C:
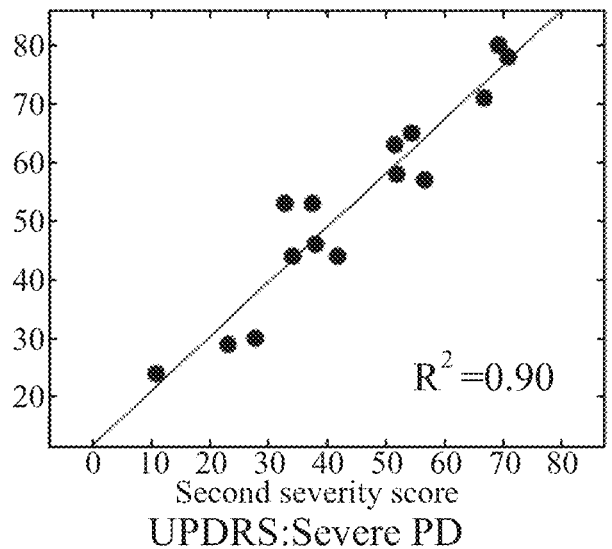
Figure 9A:
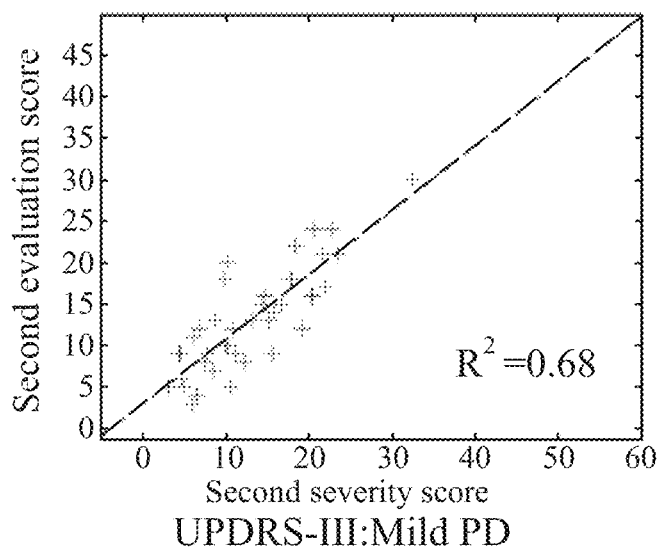
FIGS. 9(a) to 9(c) are scatter plots exemplifying goodness of fit of a linear regression model for predicting a prognosis of PD in UPDRS-III according to the method of this disclosure.
Figure 9B:
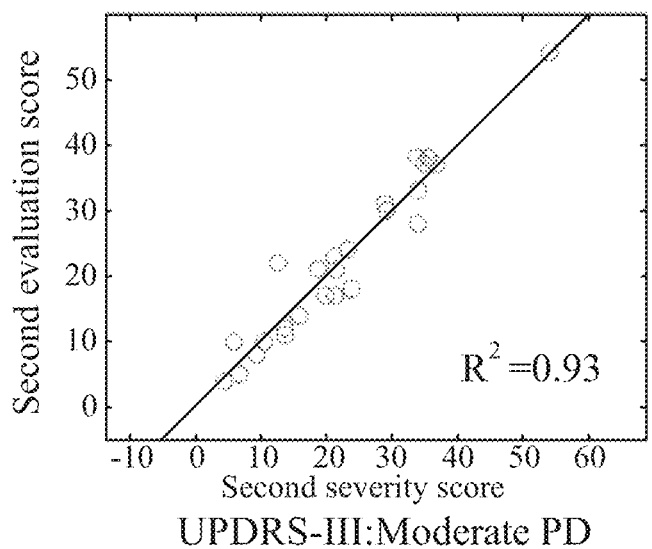
Figure 9C:
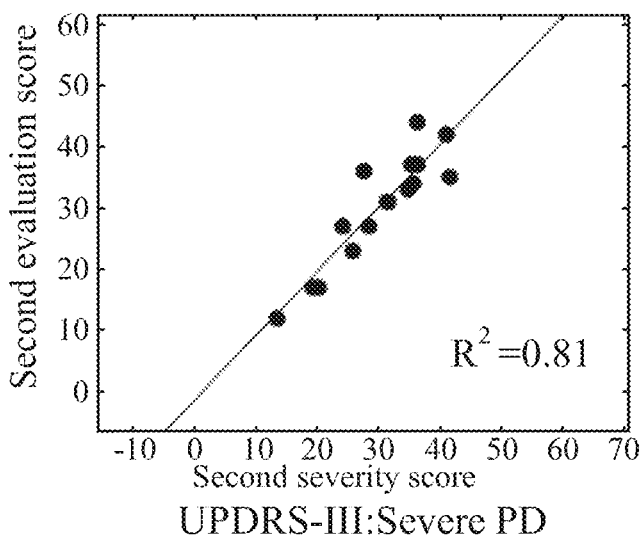

Similarly, a plurality of samples, each of which is associated with a PD patient, are collected and analyzed. Specifically speaking, each of the samples includes a plurality of diffusion MRI images 2 and an anatomical image 3 of the PD patient generated at a first time instance, first evaluation scores obtained through filling in, by the PD patient at around the same time as the first time instance, assessment forms of mild, moderate and sever rating scales in UPDRS, and second evaluation scores obtained through filling in, by the PD patient at a second time instance, assessment forms of mild, moderate and sever rating scales in UPDRS. The second severity scores are calculated by the linear regression model of this disclosure based on the samples thus collected and on the first evaluation scores. Subsequently, an adjusted $R^2$ is utilized to inspect the goodness of fit of the predication model mentioned above (i.e., the linear regression model) for predicting the second evaluation scores in the mild, moderate and sever rating scales in UPDRS. Referring to FIGS. 8(a) to 8(c), it is evident that the linear regression model of this disclosure is also suitable for use in estimating a prognosis of PD of a brain previously examined. In each of FIGS. 8(a) to 8(c), an adjusted $R^2$ is equal to a respective one of 0.63, 0.90 and 0.90. Likewise, referring to each of FIGS. 9(a) to 9(c), an adjusted $R^2$ is equal to a respective one of 0.68, 0.93 and 0.81, and is utilized to inspect the goodness of fit of the prediction model mentioned above (i.e., the linear regression model) for predicting, based on first evaluation scores obtained through filling in, by the PD patient, assessment forms of mild, moderate and sever rating scales in Unified Parkinson's Disease Rating Scale —motor domain (UPDRS-III) at a first time instance, second evaluation scores that would otherwise be obtained through filling in, by the PD patient, assessment forms of mild, moderate and sever rating scales in UPDRS-III at a second time instance. The second time instance is later than the first time instance by one year.

Figure 10:
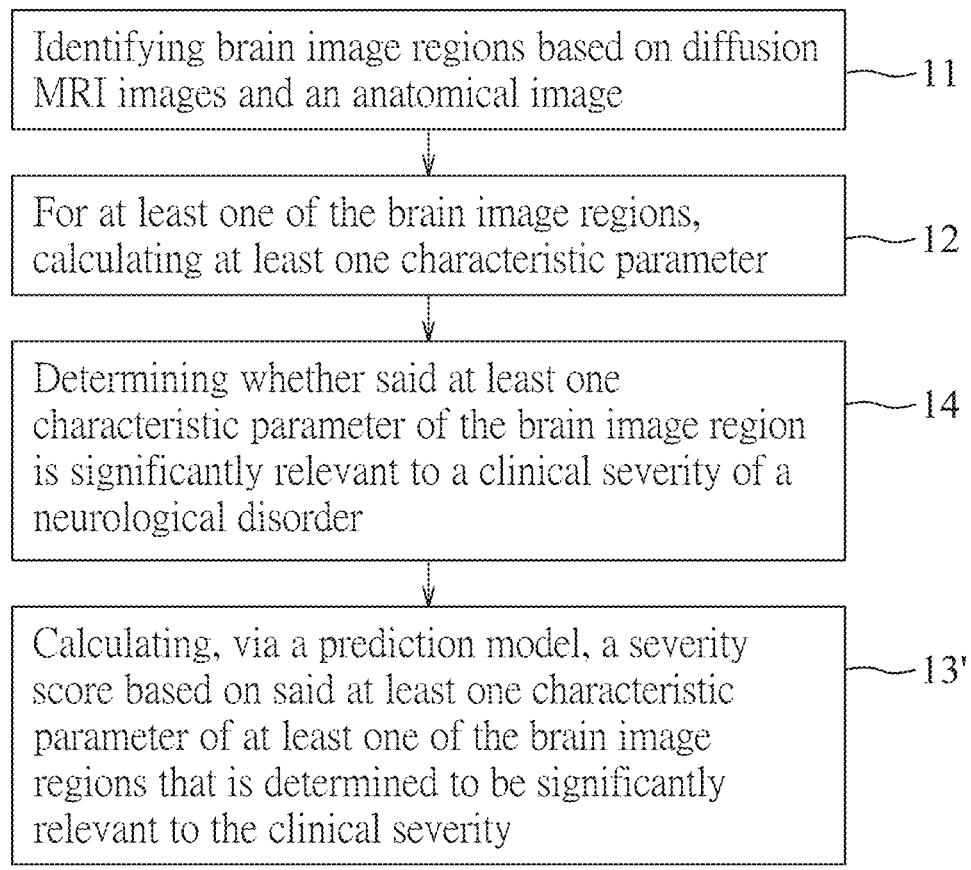
FIG. 10 illustrates a flow diagram of another embodiment of the method according to the disclosure.

In one embodiment, prior to training the linear regression model, for each of the brain image regions 4 of each training sample, a statistical correlation analysis (e.g., by using Pearson's correlation coefficient) is utilized to determine whether said at least one characteristic parameter of the brain image region 4 is significantly relevant to the clinical severity of the neurological disorder. Thereafter, in training the linear regression model, merely the characteristic parameters of the brain image regions 4 which are determined to be significantly relevant to the clinical severity are utilized for training. Moreover, as shown in FIG. 10, when estimating the clinical severity of a neurological disorder, the severity score can be calculated in step 13' based on the characteristic parameters of the brain image regions 4 which are determined to be significantly relevant to the clinical severity in step 14. It should be noted that the statistical correlation analysis and the automatic selection of the characteristic parameters by the statistical approach are independently performed so as to cooperatively reduce the number of the characteristic parameters actually required for training the prediction model and/or calculating the severity score.

In one embodiment, the severity score can be calculated by other implementations of the prediction model. For instance, a plurality of training samples corresponding to a neurological disorder can be collected in advance to train an artificial neural network, and then the artificial neural network can be utilized to serve as the prediction model for the severity score calculation.

In summary, the method of this disclosure includes identifying brain image regions according to diffusion MRI images and an anatomical image which are associated with a brain. In addition, the method further includes calculating, for at least one diffusion index of each of the brain image regions, at least one characteristic parameter based on the index values of said at least one diffusion index, and determining clinical severity of a neurological disorder, via a prediction model previously trained, based on the characteristic parameters thus calculated. As a result, the severity score representing the clinical severity of the neurological disorder can be effectively determined.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for determining a clinical severity of a neurological disorder based on at least one magnetic resonance imaging (MRI) image of a brain examined for an individual having the neurological disorder, the method being to be implemented by a computing device, the method comprising:
   a) training in advance, a prediction model that is associated with the neurological disorder, wherein the training of the prediction model is performed using training data,
      wherein the training data includes a plurality of samples corresponding to the neurological disorder, each sample of the plurality of samples including: a plurality of diffusion MRI images of the brain of the individual, an anatomical image of the brain of the individual, and at least one evaluation score determined from at least one assessment form manually completed by the individual during a time period when the plurality of diffusion MRI images and the anatomical image of the brain of the individual were generated;
   b) identifying, based on the at least one MRI image, a plurality of brain image regions each of which contains a respective portion of diffusion index values of at least one diffusion index, wherein the at least one diffusion index is determined from a result of image processing performed on the at least one MRI image;
   c) calculating, for at least one of the plurality of brain image regions, at least one characteristic parameter based on the respective portion of the diffusion index values of the at least one diffusion index;
   d) determining clinical relevancy for the at least one characteristic parameter for each of the plurality of brain image regions, wherein the clinical relevancy is determined by statistical correlation analysis;
   e) calculating a severity score that represents the clinical severity of the neurological disorder of the brain examined based on the at least one characteristic parameter of the at least one of the plurality of brain image regions via the trained prediction model,
   wherein in step e) the prediction model is a linear regression model,
   wherein step e) includes substituting the at least one characteristic parameter of the at least one of the plurality of brain image regions as at least one independent variable of the linear regression model to calculate a dependent variable of the linear regression model as the severity score,
   wherein the neurological disorder includes one of Parkinson's disease (PD), Alzheimer's disease (AD), cerebral palsy (CP) and combinations thereof, and
   wherein in step c), for each of the brain image regions, the at least one characteristic parameter includes a statistical value of the respective portion of the diffusion index values of the at least one diffusion index,
   the method further comprising
   wherein step e) includes calculating the severity score based on the at least one characteristic parameter of the at least one of the plurality of brain image regions which are determined in step d) to be relevant to the clinical severity.

2. The method as claimed in claim 1, wherein in step e), the severity score is associated with the brain in a time period during which the at least one MRI image of the brain examined is generated.

3. The method as claimed in claim 1, wherein in step c), the respective portion of the diffusion index values is a statistical value and is one of a percentile and a mean.

4. The method as claimed in claim 1, wherein in step b), the image processing is one of diffusion tensor imaging (DTI), diffusion kurtosis imaging (DKI), neurite orientation dispersion and density imaging (NODDI), and an AxCaliber technique.

5. The method as claimed in claim 1, wherein step b) includes sub-steps of:
   fitting a diffusion model to the at least one MRI image to result in said at least one diffusion index;
   normalizing said at least one diffusion index based on an anatomical image and a structural template; and
   parcellating said at least one diffusion index thus normalized through automatic whole-brain parcellation according to a standard brain parcellation template.

* * * * *